US008187889B2

(12) United States Patent
Lomnytska et al.

(10) Patent No.: US 8,187,889 B2
(45) Date of Patent: May 29, 2012

(54) PROTEIN MARKERS FOR THE DIAGNOSIS AND PROGNOSIS OF OVARIAN AND BREAST CANCER

(75) Inventors: Marta Lomnytska, Lviv (UA); Anna Dubrovska, San Diego, CA (US); Ulf Hellman, Uppsala (SE); Nataliya Volodko, Lviv (UA); Serhiy Souchelnytskyi, Uppsala (SE)

(73) Assignee: Ludwig Institute For Cancer Research Ltd., New York, NY (US)

( * ) Notice: Subject to any disclaimer, the term of this patent is extended or adjusted under 35 U.S.C. 154(b) by 0 days.

(21) Appl. No.: 11/829,360

(22) Filed: Jul. 27, 2007

(65) Prior Publication Data

US 2008/0213907 A1    Sep. 4, 2008

Related U.S. Application Data

(60) Provisional application No. 60/834,309, filed on Jul. 27, 2006.

(51) Int. Cl.
*G01N 33/574* (2006.01)
*C07K 16/30* (2006.01)

(52) U.S. Cl. ............... 436/64; 436/63; 436/65; 530/350; 530/387.7; 530/388.15; 506/18; 506/17

(58) Field of Classification Search .................... 436/64, 436/63, 65; 530/350, 387.7, 388.15; 506/17, 506/18
See application file for complete search history.

(56) References Cited

U.S. PATENT DOCUMENTS

2006/0211009 A1*  9/2006  An et al. ........................ 435/6

OTHER PUBLICATIONS

Anderson, et al., "The Human Plasma Proteome: History, Character, and Diagnostic Prospects," Molecular & Cellular Proteomics 1.11, 2002, vol. 1, pp. 845-867.
Anderson, et al., "The Human Plasma Proteome: A Nonredundant List Developed by Combination of Four Separate Sources," Molecular & Cellular Proteomics 3.4, 2004, vol. 3, pp. 311-326.
Sidransky, David, "Emerging Molecular Markers of Cancer," Nature Reviews/Cancer, 2002, vol. 2, pp. 210-219.
Le Naour, et al., "Proteomics-based Identification of RS/DJ-1 as a Novel Circulating Tumor Antigen in Breast Cancer," Clinical Cancer Research, 2001, vol. 7, pp. 3328-3335.
Cohen, et al., "Three-Dimensional Power Doppler Ultrasound Improves the Diagnostic Accuracy for Ovarian Cancer Prediction," Gynecologic Oncology, 2001, vol. 82, pp. 40-48.
Luo, et al., "The Serum Concentration of Human Kallikrein 10 Represents a Novel Biomarker for Ovarian Cancer Diagnosis and Prognosis," Cancer Research, 2003, vol. 63, pp. 807-811.

(Continued)

*Primary Examiner* — Krishnan S Menon
*Assistant Examiner* — Rebecca M Fritchman
(74) *Attorney, Agent, or Firm* — White & Case LLP

(57) ABSTRACT

Plasma samples of ovarian and breast cancer patients were used to search for markers of cancer, using two-dimensional gel electrophoresis and MALDI TOF mass spectrometry. Truncated forms of cytosolic serine hydroxymethyl transferase (cSHMT), T-box transcription factor 3 (Tbx3) and utrophin were aberrantly expressed in samples from cancer patients, as compared to samples from noncancer cases. Aberrant expression of proteins was validated by immunoblotting of plasma samples with specific antibodies to cSHMT, Tbx3 and utrophin. A cohort of 79 breast and 39 ovarian cancer patients, and 31 individuals who were either healthy or had noncancerous conditions was studied. We observed increased expression of truncated cSHMT, Tbx3 and utrophin in plasma samples obtained from patients at early stages of disease. The results indicate that cSHMT, Tbx3, utrophin and truncated forms thereof can be used as components of multiparameter monitoring of ovarian and breast cancer.

4 Claims, 10 Drawing Sheets

OTHER PUBLICATIONS

Zhang, et al., "Three Biomarkers Identified from Serum Proteomic Analysis for the Detection of Early Stage Ovarian Cancer," Cancer Research, 2004, vol. 64, pp. 5882-5890.

Ahmed, et al., "Proteomic-Based Identification of Haptoglobin-1 Precursor as a Novel Circulating Biomarker of Ovarian Cancer," British Journal of Cancer, 2004, vol. 91, pp. 129-140.

Petricoin, et al., "Use of Proteomic Patterns in Serum to Identify Ovarian Cancer," The Lancet, 2002, vol. 359, pp. 572-577.

Kanamoto, et al., "Functional Proteomics of Transforming Growth Factor-$\beta$1-Stimulated Mv1Lu Epithelial Cells: Rad51 as a Target of TGF$\beta$1-Dependent Regulation of DNA Repair," The EMBO Journal, 2002, vol. 21, No. 5, pp. 1219-1230.

Lomnytska, et al., "Transforming Growth Factor-$\beta$1-Regulated Proteins in Human Endothelial Cells Identified by Two-Dimensional Gel Electrophoresis and Mass Spectrometry," Proteomics, 2004, vol. 4, pp. 995-1006.

Kaplan, et al., "Nonparametric Estimation from Incomplete Observations," J. Am. Stat. Assoc., 1958, vol. 53, pp. 457-481.

Blake, et al., "Function and Genetics of Dystrophin and Dystrophin-Related Proteins in Muscle," Physiol. Rev., 2002, vol. 82, pp. 291-329.

Chen, et al., "Polymorphisms in the One-Carbon Metabolic Pathway, Plasma Folate Levels and Colorectal Cancer in a Prospective Study," Int. J. Cancer, 2004, vol. 110, pp. 617-620.

Bamshad, et al., "Mutations in Human TBX3 Alter Limb, Apocrine and Genital Development in Ulnar-Mammary Syndrome," Nature Genetics, 1997, vol. 16, pp. 311-315.

Van't Veer, et al., "Gene Expression Profiling Predicts Clinical Outcome of Breast Cancer," Nature, 2002, vol. 415, pp. 530-536.

Kreunin, et al., "Identification of Metastasis-Associated Proteins in a Human Tumor Metastasis Model Using the Mass-Mapping Technique," Proteomics, 2004, vol. 4 (9), pp. 2754-2765.

Brummelkamp, et al., "TBX-3, the Gene Mutated in Ulnar-Mammary Syndrome, Is a Negative Regulator of p19$ARF$ and Inhibits Senescence," The Journal of Biological Chemistry, 2002, vol. 277, No. 8, pp. 6567-6572.

Henry, et al., "Reduced Expression of Dystroglycan in Breast and Prostate Cancer," Human Pathology, 2001, vol. 32, No. 8, pp. 791-795.

Jones, et al., "Proteomic Analysis and Identification of New Biomarkers and Therapeutic Targets for Invasive Ovarian Cancer," Proteomics, 2002, vol. 2, pp. 76-84.

Esteva, et al., "Prognostic Molecular Markers in Early Breast Cancer," Breast Cancer Research, 2004, vol. 6, No. 3, pp. 109-118.

Lomnytska, et al., "Increased expression of cSHMT, Tbx3 and utrophin in plasma of ovarian and breast cancer patients," Int. J. Cancer: 118, 412-421 (2006).

* cited by examiner

Figure 1A, B
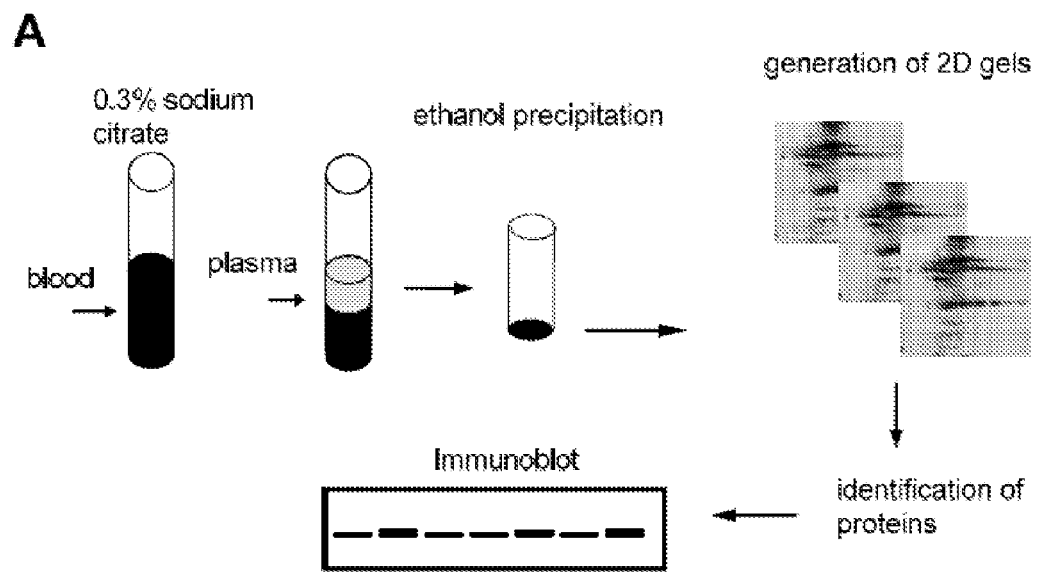
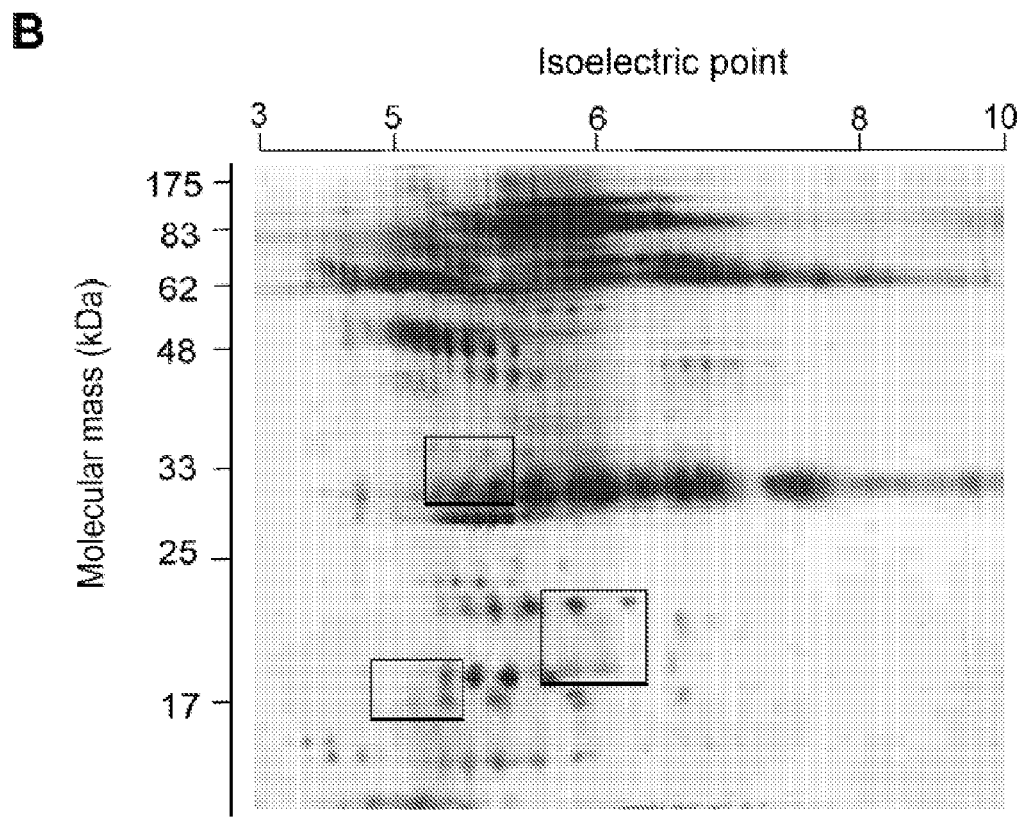

Figure 7. Overall survival of ovarian cancer patients (n=39, follow-up period – 48 months), in relation to cSHMT expression in plasma (Kaplan-Meier univariate analysis).

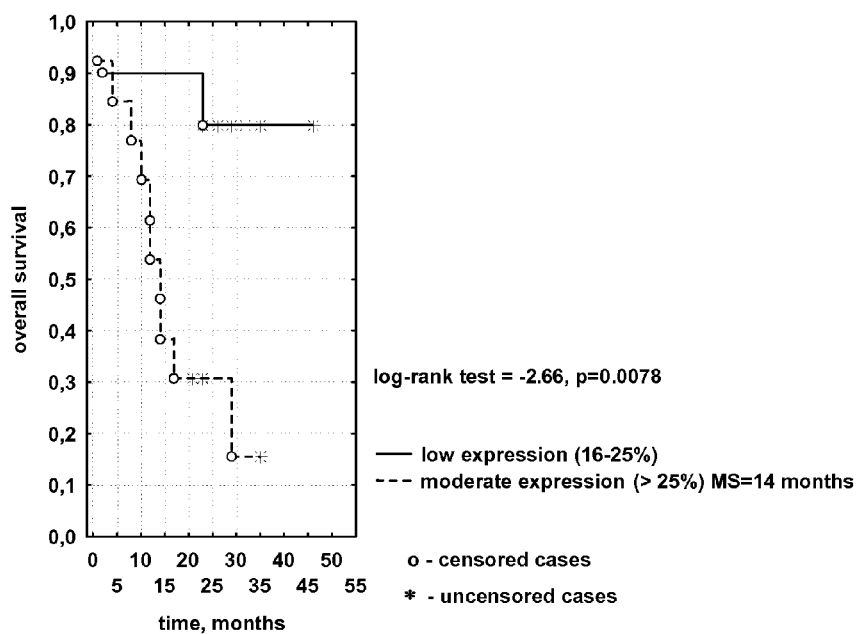

The expression of the cSHMT was calculated as ratio (%) between the levels of cSHMT and immunoglobulins in plasma, as evaluated by immunoblotting.
The expression of the cSHMT in blood plasma of healthy women and women with noncancerous cases was ≤ 10%.
The expression level of cSHMT in plasma <16% was considered to be negative.
The expression level of cSHMT in plasma between 16 and 25% was considered as low.
The expression level of cSHMT in plasma >25% was considered as moderate.

Figure 8. Overall survival of breast cancer patients (n=50, follow-up period – 48 months), in relation to Tbx3 expression in plasma (Kaplan-Meier univariate analysis).

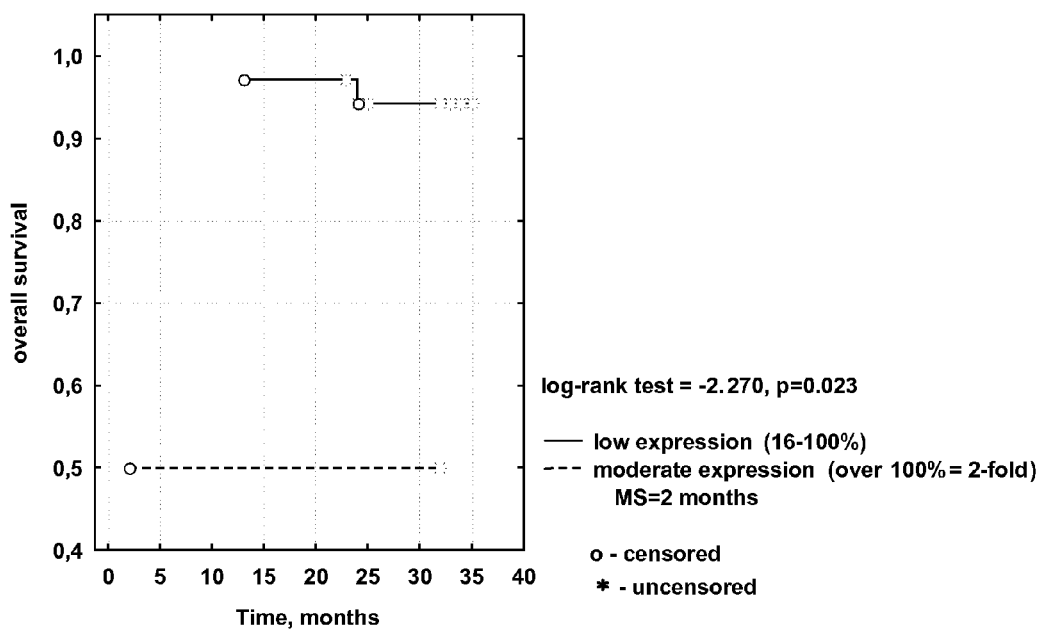

The expression of the Tbx3 was calculated as ratio (%) between the levels of Tbx3 and immunoglobulins in plasma, as evaluated by immunoblotting.

The expression of Tbx3 in blood plasma of healthy women and women with noncancerous conditions was ≤ 15%.

The expression level of Tbx3 in plasma ≤15% was considered as negative.
The expression level of Tbx3 in plasma between 16 and 100% was considered as low.
The expression level of Tbx3 in plasma ≥100% was considered as moderate.

Figure 9. Overall survival of breast cancer patients (n=55, follow-up period – 48 months), in relation to expression of utrophin in plasma (Kaplan-Meier univariate analysis).

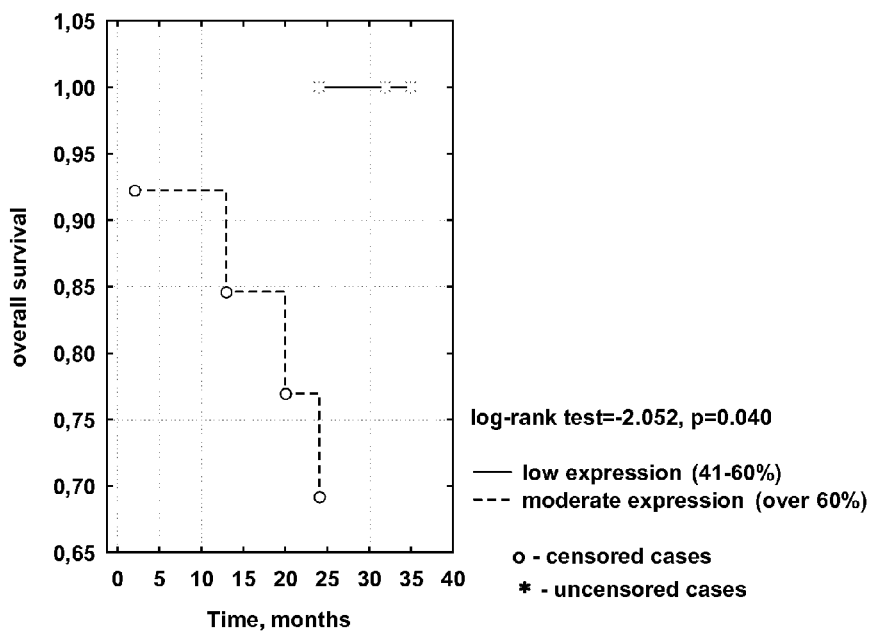

The expression of the utrophin was calculated as ratio (%) between the levels of the utrophin and immunoglobulins in plasma, as evaluated by immunoblotting.
The expression of the utrophin in blood plasma of healthy women and women with noncancerous cases was ≤ 36%.
The expression level of the utrophin in plasma ≤40% was considered as negative.
The expression level of the utrophin in plasma between 41 and 60% was considered as low.
The expression level of the utrophin in plasma ≥60% was considered as moderate.

PROTEIN MARKERS FOR THE DIAGNOSIS AND PROGNOSIS OF OVARIAN AND BREAST CANCER

This application claims the benefit of U.S. Provisional Application No. 60/834,309, filed Jul. 27, 2006.

FIELD OF THE INVENTION

The present invention is directed to the field of cancer detection and diagnosis. More particularly, it is directed to new protein markers and their use in diagnosing and monitoring ovarian and breast cancer.

BACKGROUND OF THE INVENTION

Blood plasma is an easily accessible source of proteins which have diagnostic value, as it is in contact with practically all tissues in the human body. Plasma proteome contains not only proteins which function in or via plasma, e.g. albumin, immunoglobulins and cytokines, but also proteins which leak from tissues.[1] During tumor growth, damage of normal or tumor tissues leads to release of cellular proteins into plasma. Currently, 196 proteins have been identified in human plasma, but up to 1175 distinct gene products may be present in human plasma.[2]

Plasma has been extensively explored in searches for markers of tumorigenesis. However, attempts to find a single reliable early marker of human breast or ovarian cancer have not been fully successful. Variability of molecular mechanisms governing tumor growth and its spreading in the body indicates that an expression pattern of a few markers may be more informative than a single marker.[3,9,16] This prompts a search for proteins which change their expression in an accessible diagnostic material, e.g. blood. Two-dimensional gel electrophoresis (2D-GE), liquid chromatography and mass spectrometry, as well as various array techniques have been used.[3] Among described markers, CA125, CA15-3, CEA, and RS/DJ1 proteins have been proposed as useful markers to monitor breast cancer.[3,4] CA125, apolipoprotein A1, transthyretin, inter-α trypsin inhibitor heavy chain H4, haptoglobin-1 and kallikrein have been proposed as markers of ovarian cancer.[5-8] None of the identified protein markers has been found to predict cancer appearance and development with a probability value close to 100%. This can be explained by the presence of these proteins in normal nontransformed cells, as well as in tumor cells; in tumors, marker proteins change their activities or relocalize in cells.

A combination of a few markers was proposed to predict the appearance and development of tumors with higher accuracy, as compared to use of a single marker. The application of surface-enhanced laser desorption/ionization mass spectrometry (SELDI) provides one means of implementing such a multiparameter approach.[9] A combination of identified markers would be the most preferable solution for such multiparameter diagnostics. However, SELDI does not provide identities of proteins or peptides in identified mass peaks.

Cytoplasmic serine hydroxymethyl transferase (cSHMT) is one of the key enzymes of one-carbon metabolism, the pathway which is altered in colorectal cancer.[14] Increased expression of cSHMT has been found in metastatic human breast carcinoma cells MDA-MB-435, as compared to non-metastatic cells.[17] Whether cSHMT function is affected in breast and ovarian cancers remains to be investigated. T-box transcription factor 3 (Tbx3), on the contrary, is involved in development of mammary gland; mutations or lack of Tbx3 result in mammary hypoplasia, and even in lack of mammary glands.[15] Tbx3 has been described as a potent inhibitor of senescence of neuronal cells and embryonal fibroblasts.[18] Utrophin has been described first as a protein involved in development of neuromuscular junctions. However, utrophin detection in a variety of cells has indicated its role in organization of connections between cytoskeleton and transmembrane proteins. Utrophin has a number of splicing forms, and a variety of short isoforms have been described.[13] Utrophin has been detected in mammary ductal epithelium and in stroma.[19] Expressions of utrophin and its binding partner dystroglycan were found to be reduced in breast adenocarcinomas.[19] It is possible that the decrease of utrophin in cells is accompanied by release of this protein into the plasma. cSHMT, Tbx3 and utrophin are known to function inside of cells, and their appearance in plasma in truncated forms suggests that they were released from cells and subjected to a limited proteolysis.

Herein is described the increased appearance of truncated forms of cSHMT, Tbx3 and utrophin in plasma of patients with breast and ovarian cancer. The use of these markers alone or, in a multiparameter approach, in combination with each other or in combination with other markers provides a significant development and improvement in cancer diagnostics.

SUMMARY OF THE INVENTION

The present invention is directed to new protein markers useful in the diagnosis and prognosis of ovarian and breast cancer. The terms expression, aberrant expression, etc. in the present application are used to describe the presence, amount, level or relative level of the cSHMT, Tbx3 and utrophin proteins, or truncated forms thereof, in plasma of cancer patients or patients without cancer (controls), except where specifically stated otherwise. More particularly, the invention is directed to cSHMT, Tbx3 and utrophin and truncated forms thereof, the aberrant expression of which in plasma has now been shown to correlate with increased incidence of ovarian and breast cancer. In a related vein, low levels of expression have now been associated with cancer-free patients. In a related discovery, lower levels of these proteins in cancer patients have now been correlated with increased time and chance of survival and, in a related vein, aberrant expression has now been linked to low rates and decreased times of survival. The invention is directed both to the new protein markers and to methods for detecting the onset of ovarian and beast cancer and monitoring the progress thereof. The invention is further directed to antibodies raised against the new markers and which serve as a vital component of the intended diagnostic methods.

One aspect of the invention provides a method employing the markers for diagnosis of ovarian and/or breast cancer. A plasma sample from a patient is tested for the presence and amounts of the markers, and the results indicate the presence or absence of the cancer(s).

In another aspect of the invention, the markers of the invention are used in a prognostic application. A plasma sample from a patient with ovarian and/or breast cancer is tested for the presence and amounts of the markers, and the results are correlated with duration and chance of survival.

Yet another aspect of the invention is a kit comprising antibodies raised against one or more of the markers, which kit can be used as a diagnostic and prognostic tool in connection with ovarian and/or breast cancer.

BRIEF DESCRIPTION OF THE DRAWINGS

FIG. 1A is a schematic representation of the method for identifying the protein markers of the present invention.

FIG. 1B shows a typical 2D gel illustrating the quality of protein resolution.

FIG. 7 is a graphic depiction of the correlation between expression of cSHMT in plasma and overall survival of ovarian cancer patients.

FIG. 8 is a graphic depiction of the correlation between expression of Tbx3 in plasma and overall survival of breast cancer patients.

FIG. 9 is a graphic depiction of the correlation between expression of utrophin in plasma and overall survival of breast cancer patients.

DETAILED DESCRIPTION OF THE INVENTION

Figure 1C:
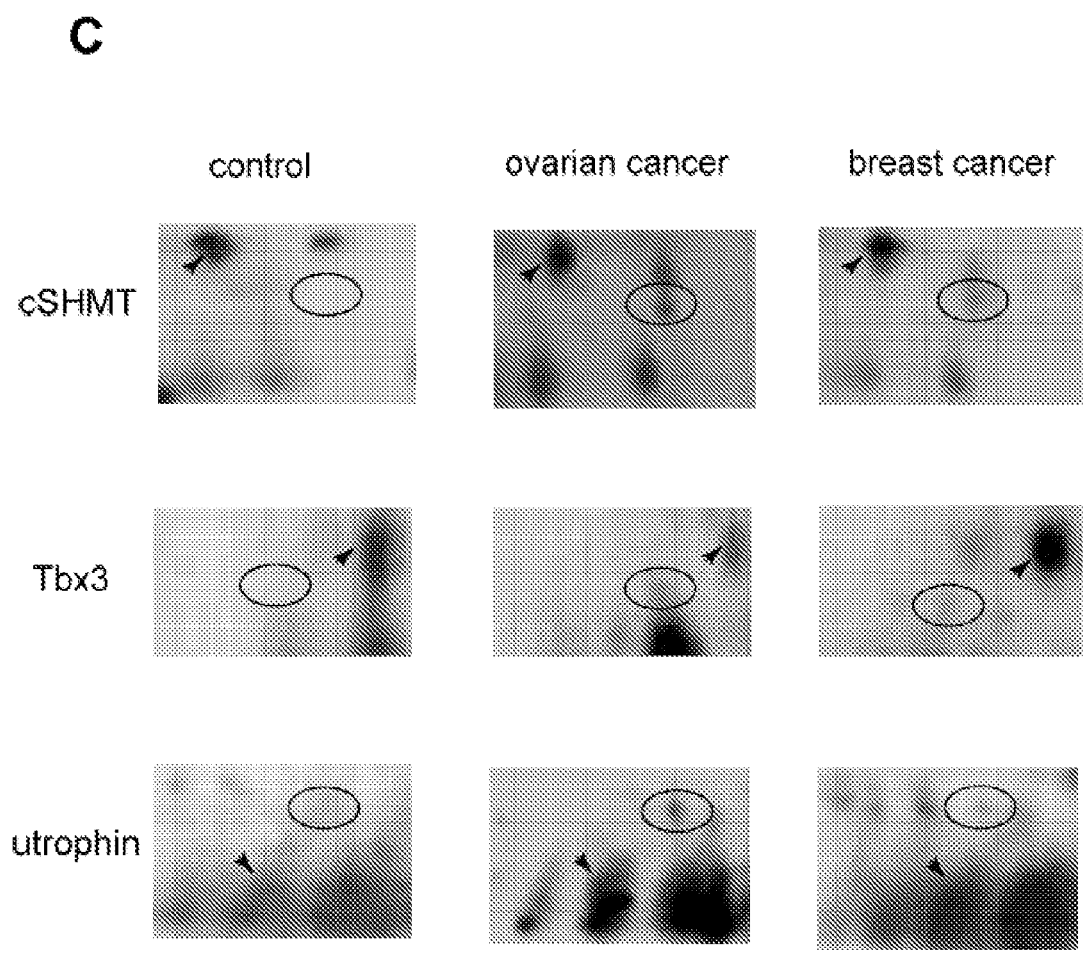
FIG. 1C shows gels showing the areas of migration of the marker proteins in noncancerous, ovarian cancer and breast cancer patients.

Material and Methods
Patient Group

Samples were collected from 79 breast cancer patients, 39 ovarian cancer patients, 28 patients with nonmalignant processes of pelvis and breast, and 3 healthy individuals (Table 1). Clinical, instrumental, histopathological diagnostics and treatment of patients were performed at the Lviv Regional Oncology Center. The information about patients was deposited in the Cancer Register database of the Lviv Regional Oncology Center. Sample collection was performed with consent of the patients, in accordance with the rules for handling of medical information and medical samples, and under supervision of the Ethical Committee of the Lviv National Medical University. Staging of patients was performed according to the Federation of Gynaecologic Oncologists (FIGO) and TNM (9th edition) classifications. Samples were coded immediately after collection, and coding was preserved throughout the study until conclusive proteomics and immunoblotting data had been generated.

Sample Preparation

Plasma protein samples were prepared from cubital venous blood; blood was collected into tubes with 0.3% sodium citrate solution. Blood was collected in the morning, before breakfast and any physical activities. Shortly after collection (10-15 min) blood was centrifuged for 10 min at 3000 rpm. Aliquots of plasma were transferred into 1.5 ml tubes and proteins were precipitated on ice with 96% ethanol (ratio 1:3; plasma:ethanol). Other ratios of plasma:ethanol (1:1, 1:5, 1:10), as well as precipitation with acetone, resulted in significantly less efficient precipitation and/or recovery of plasma proteins. The pellet was obtained by centrifugation (20 min, 13000 rpm, +4° C.). Supernatant was discarded, and plasma-precipitated proteins were air-dried and stored at room temperature in closed tubes until further analysis. We observed that precipitated plasma proteins prepared according to this protocol can be stored for up to two years without deterioration of protein recovery and resolution in two-dimensional gel electrophoresis.

Two-Dimensional Gel Electrophoresis

Samples were dissolved in 2D-GE buffer (8 M urea, 4% CHAPS, 0.5% DTT, IPG buffer pH 3-10). Samples (100 μg of protein) were subjected to isoelectric focusing (IEF) using 18 cm linear IPGDry strips with a pH range of 3-10 (Amersham Biosciences). Samples were loaded by the in-gel rehydration technique, with active loading during the last 3 h. IEF was performed in an IPGphor (Amersham Biosciences, Uppsala, Sweden) using the following protocol: rehydration, 10 h, then 50 V, 3 h; 1,000 V, 1 h; 8,000 V, 10 h; or until the total volt-hours reached 50,000. After IEF, strips were equilibrated in 50 mM Tris-HCl pH 8.8, 6 M urea, 2.0% SDS, 30% glycerol with 1% DTT for 10 min, and then for 10 min in the same buffer containing 4% iodoacetamide instead of DTT. Equilibrated strips were placed on top of 12% polyacrylamide gels and fixed with 0.5% agarose in 62.5 mM Tris-HCl pH 6.8, 0.1% SDS. Sodium dodecylsulfate polyacrylamide gel electrophoresis (SDS-PAGE) was performed in a Dalt-Six, following the manufacturer's recommendations (constant power 50 W, for 6 to 8 h; Amersham Biosciences). Gels were fixed in 10% acetic acid and 20% methanol for 10-12 h. Proteins were detected by silver staining as previously described.[10,11]

Image Analysis

Silver-stained gels were scanned in an ImageScanner with the MagicScan32 software and analyzed with calculation of volumes of spots by the ImageMaster 2D Elite software (Amersham Biosciences). Protein spots differentially expressed in cancer and noncancer patients were considered for protein identification. The statistical significance of changes was evaluated using the ImageMaster 2D Elite software.[10]

Protein Identification

Protein spots were excised from gels, destained and subjected to in-gel digestion with trypsin (modified, sequence grade porcine; Promega, Madison, Wis., USA), as described.[10,11] Tryptic peptides were concentrated and desalted on a nanocolumn. Peptides were eluted with 50% acetonitrile containing α-cyano-4-hydroxycinnamic acid as the matrix, applied directly onto the metal target and analyzed by matrix-assisted laser desorption/ionization time of flight mass spectrometry (MALDI TOF MS) on a Bruker Autoflex MALDI TOF mass spectrometer (Bruker Daltonics, Bremen, Germany). Peptide spectra were internally calibrated using trypsin autolytic peptides. To identify proteins, we searched the NCBI database using the ProFound search engine (http://65.219.84.5/service/prowl/profound.html). One miscut and partial oxidation of methionine were allowed. Probability of identification was evaluated according to the probability value (Z value) and sequence coverage. Comparison of the experimental pI and Mr values of proteins to their theoretical values was also considered.

Immunoblotting

For immunoblotting of cSHMT, Tbx3 and utrophin, aliquots of plasma, which were prepared as for 2D-GE, were dissolved in an SDS-PAGE sample buffer and 0.5-1.0 μg of plasma protein was subjected to 1D SDS-PAGE. After transfer to nitrocellulose membrane, proteins of interest were detected with specific antibodies: cSHMT with D-20 antibody (sc-25060, which recognizes an epitope within the C-terminal part of cSHMT), Tbx3 with C-20 antibody (sc-17872, which recognizes an epitope within the internal region of Tbx3) and utrophin with N-19 antibody (sc-7460, which recognizes an epitope within the N-terminal part of utrophin). All antibodies were from Santa Cruz Biotechnology, Santa Cruz, Calif., USA. Protein loading was controlled by internal expression of plasma immunoglobulins, and by reprobing the same membranes with anti-human IgG (ab6858, Abcam Ltd, Cambridge, UK). Proteins of interest were detected by ECL as previously described.[10,11] Intensity of detected bands was measured using a CCD camera (LAS-1000 CH, Fuji, Japan), and dedicated programs (Scion Image beta 4.0.2, Scion Corp., Frederick, Md., USA, and AIDA, Raytest IMG, Sprockhofel, Germany). Intensities of IgG bands were measured after reprobing with antihuman IgG the same membranes which were first probed with anti-cSHMT, anti-Tbx3 and antiutrophin antibodies.

Relative expressions of cSHMT, Tbx3 and utrophin in plasma were calculated as the ratio of values of a signal from cSHMT-, Tbx3- or utrophin-specific bands to IgG signal. For definition of weak, medium and strong expression, intensities of specific bands in immunoblots with antibodies to cSHMT, Tbx3 and utrophin were considered. Then, average ratio of intensities of specific protein to IgG bands in the same sample were calculated to define weak, medium and strong specific protein bands. As IgG bands were on average stronger, as compared to intensities of specific proteins, consistently shorter (though equal for all blots) exposure time for IgG immunoblotting was used. This explains the values of the ratios. These ratios were taken as cutpoints for representation of relative expression of cSHMT, Tbx3 and utrophin. The cutpoints were defined as follows. For cSHMT: weak expression, less than 25%; medium expression, 26%-50%; strong expression, more than 50%. For Tbx3: weak expression, less than 40%; medium expression, 41%-60%; strong expression, more than 61%. For utrophin: weak expression, less than 40%; medium expression, 41%-70%; strong expression, more than 71%. These ratios were used for the correlation analysis of expression of studied proteins in plasma with stages of disease.

Clinical information was available from the Department of Oncology and Radiology of the Lviv National Medical University at the Lviv Oncology Center. Results of the correlation analysis were expressed as a percentage of cases with weak, medium or strong expression of studied proteins. Sensitivity was calculated as a ratio of number of cases with detection of specific aberrantly expressed proteins to total number of cancer cases. Specificity was calculated as a ratio of cases with negative detection of specific aberrantly expressed proteins to total number of control noncancer cases.

Figure 2:
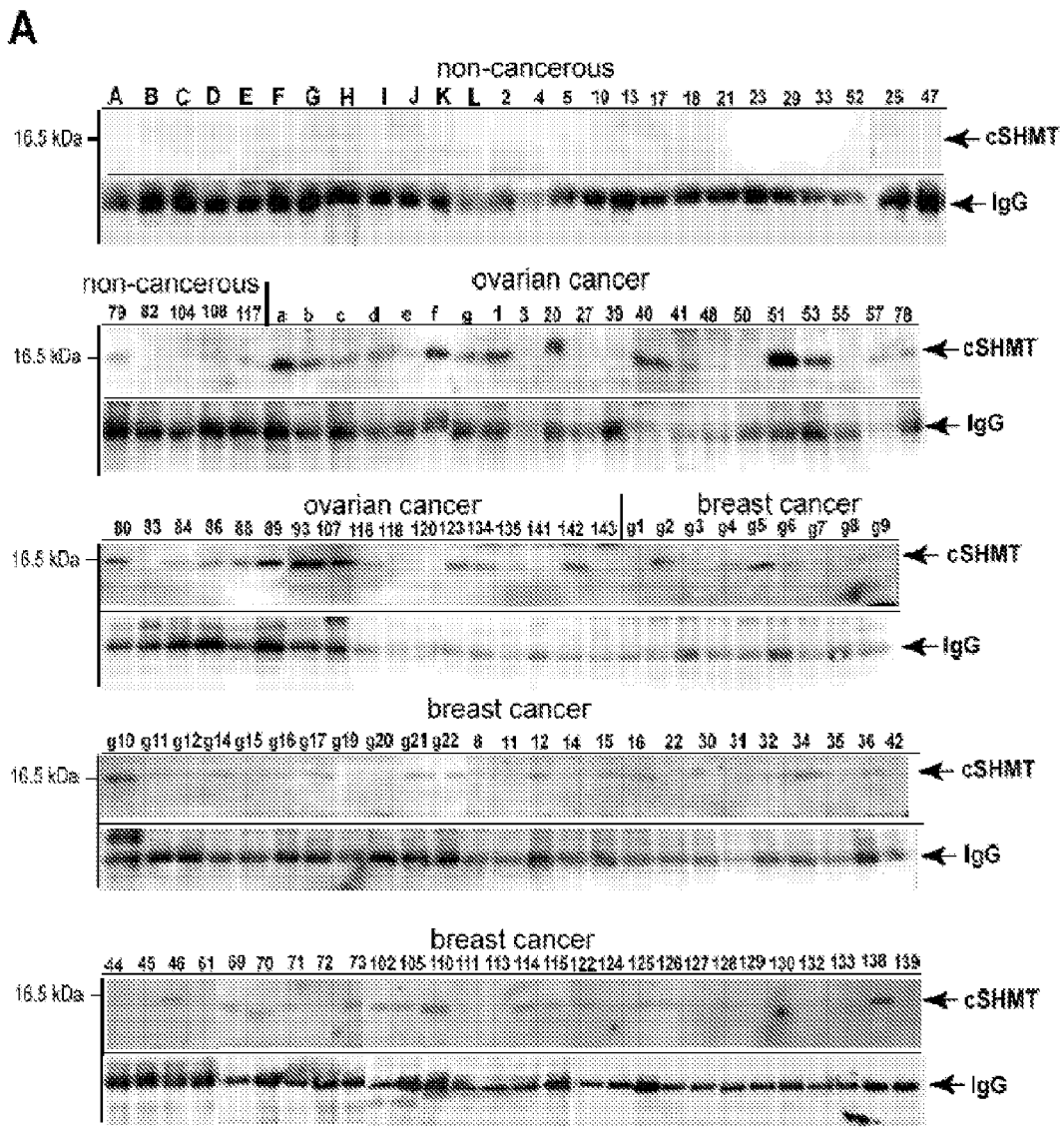
FIGS. 2A-C show various aspects of the detection of cSHMT in plasma samples by immunoblotting.
Figure 2:
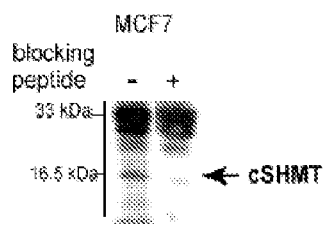
Figure 2:
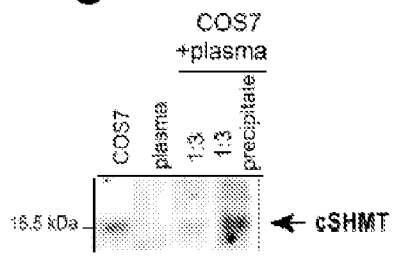
Figure 3:
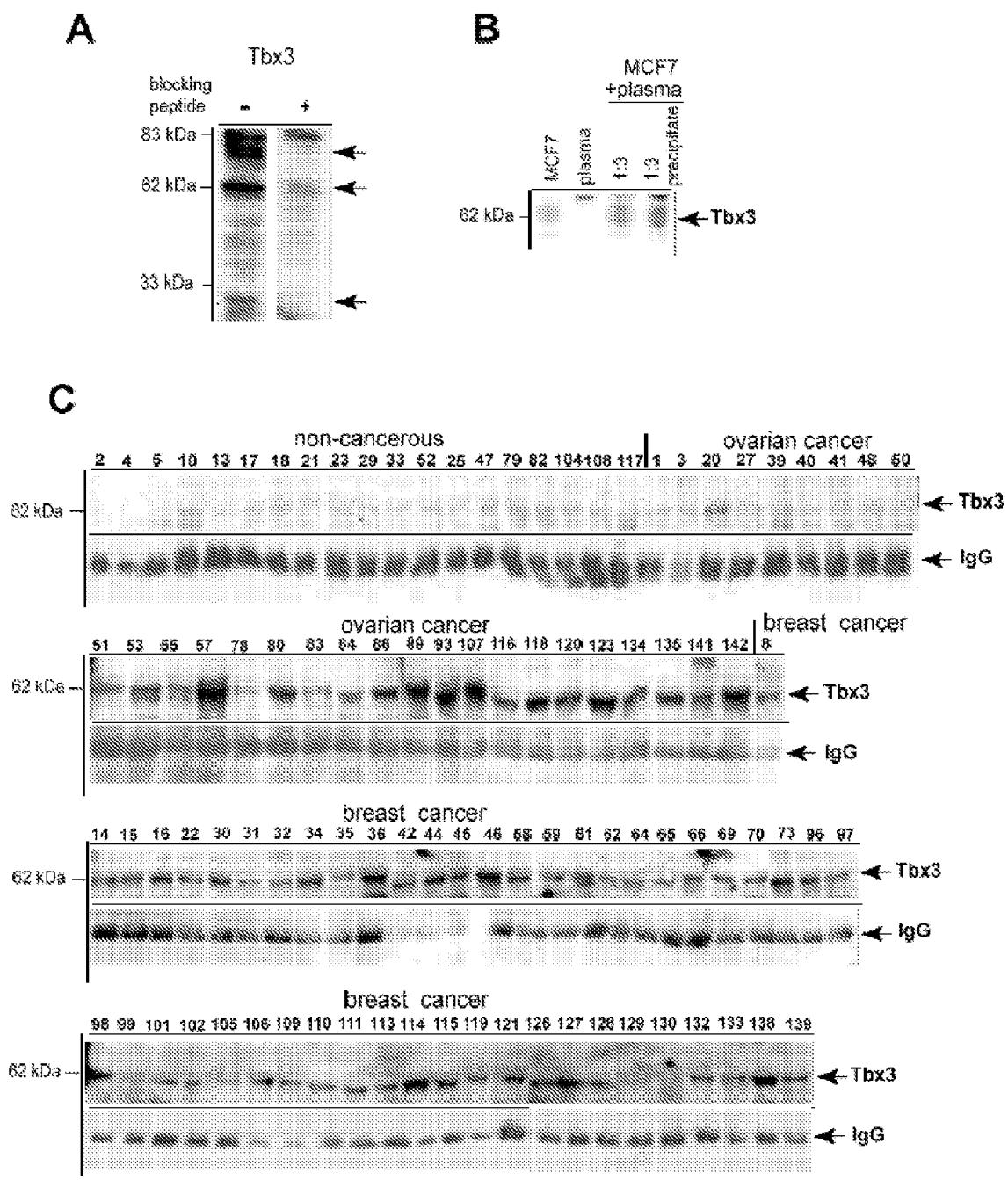
FIGS. 3A-C show various aspects of the detection of Tbx3 in plasma samples by immunoblotting.
Figure 4:
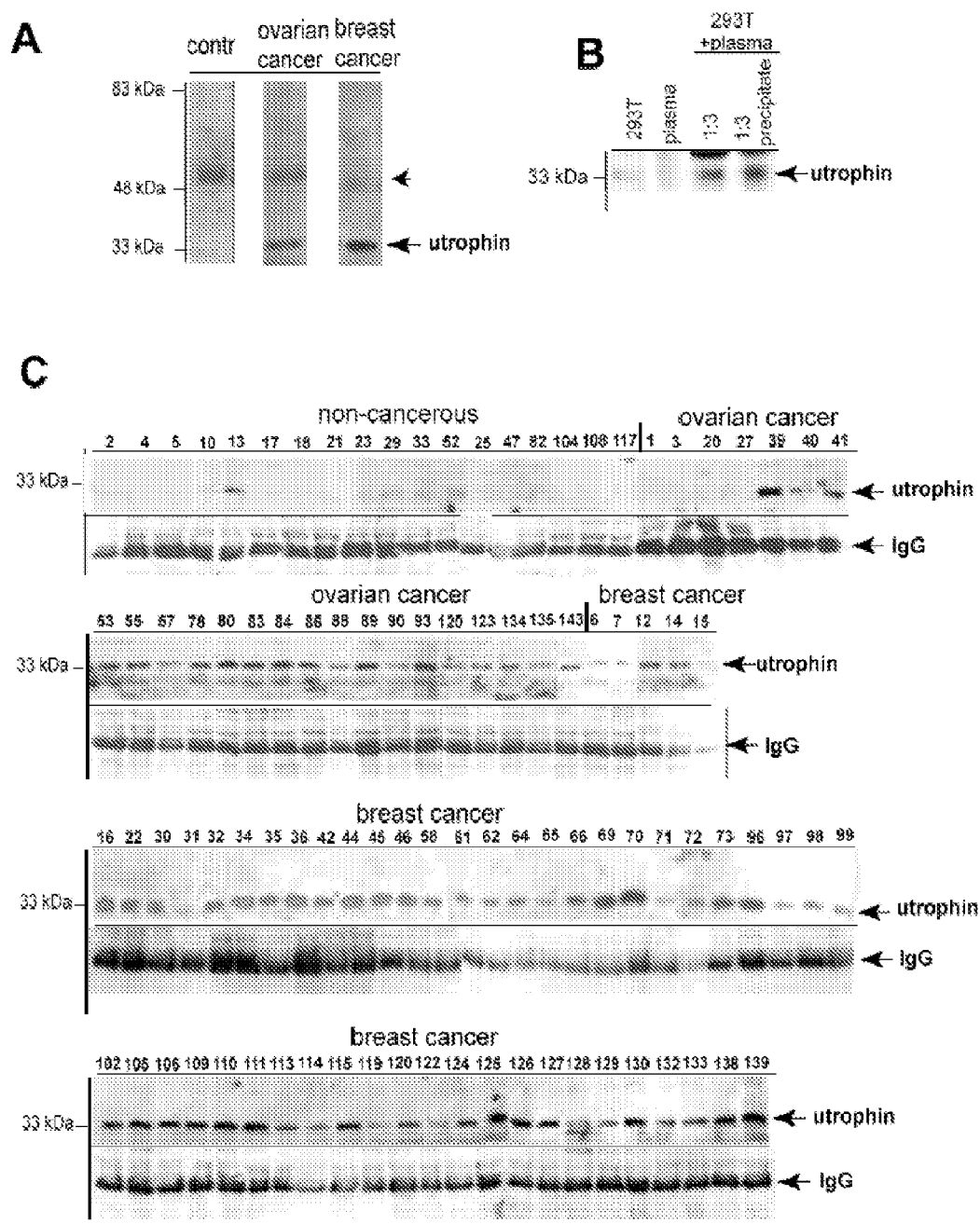
FIGS. 4A-C show various aspects of the detection of utrophin in plasma samples by immunoblotting.

For detection of cSHMT, Tbx3 and utrophin in cultured cells, we performed immunoblotting assays with whole-cell extracts as described above for plasma samples. To evaluate origin of cSHMT, Tbx3 and utrophin in plasma, we immunoblotted aliquots of cell extracts, plasma and mixture of cell extracts with plasma (ratio 1:3, cell extract to plasma, respectively; 1 h incubation) with respective specific antibodies, as indicated in FIGS. 2, 3 and 4.

Correlation analysis of cSHMT expression and survival of patients with ovarian cancer was performed by univariate Kaplan-Meier survival analysis[12] using the Statistica software (v. 6.0, StatSoft, Inc., Tulsa, USA). We used this method for evaluation of cumulative proportional overall survival of ovarian cancer patients, who were divided into two groups according to the level of expression of cSHMT in plasma.

Results

Preparation of Samples and Two-Dimensional Gel Electrophoresis of Plasma

To ensure reliability in sample preparation, we established a procedure for collection of human plasma as described previously herein. This procedure is based on ethanol precipitation of aliquots of freshly collected sodium citrated plasma. Dried protein precipitates can be stored for further analysis (FIG. 1A). This procedure is also compatible with 2D-GE. A procedure similar to the one developed by us was approved by the Human Plasma Initiative group of the Human Proteome Organization (www.hupo.org).

Collected plasma samples were subjected to 2D-GE (FIG. 1B). The interference with protein migration due to serum albumin and immunoglobulins was observed only upon loading of gels with more than 150 µg of proteins. Upon loading of 100 µg of proteins or less, perturbation of the protein migration was limited. Accordingly, plasma was not depleted from the albumin and immunoglobulins. Elimination of the depletion procedure increased reproducibility of sample preparation, as additional steps in plasma manipulation were excluded. The simplicity of the developed sample preparation procedure also facilitates its use at the clinic.

Twenty-one samples from breast cancer patients, 14 samples from ovarian cancer patients, and 10 samples from individuals without cancer were subjected to 2D-GE. Images of silver-stained gels were analyzed, and on average 700 protein spots were observed in each gel. The variation between the numbers of protein spots in gels of the same sample was below 10% of the total number of spots. If protein spots appeared in 2D gels of one or only a few samples, it was considered as individual variation, and spots were not considered for analysis. Only protein spots which were present and/or changed their expression in more than 80% of samples representing a single clinical group of patients were considered for further analysis. In total, 45 2D gels were generated, with repeating of 2D-GE of the same samples. These repeats were performed to exclude experimental variations and to select for further analysis only reproducibly detected protein spots.

Three proteins with different expression levels in plasma of cancer and noncancer individuals were identified as cSHMT, Tbx3 and utrophin (FIG. 1C; Table 2). It should be noted that migration positions in 2D gels of identified proteins indicated lower molecular masses than would be expected for the full-length proteins (Table 2). By peptide mass fingerprinting, a 52 kDa isoform of Tbx3 was identified, but in 2D gels it was observed as a 17 kDa protein. We observed, however, that the peptides which were used for identification originated from the central part of the protein. This indicated that we had observed a truncated form of Tbx3 and that for a validation study, an antibody to the internal region of Tbx3 had to be used. The full-length utrophin was described as a large 395 kDa protein, but a number of splice forms of low molecular mass have been identified.[13] For a validation study, an antibody which recognizes an epitope in the N-terminal part of utrophin was used. For cSHMT, lack of the N-terminal peptides also indicated truncation which resulted in a protein of lower molecular mass, and which corresponded to the protein spot observed in 2D gels (FIG. 1). This prompted us to use an antibody to an epitope in the C-terminal part of cSHMT. cSHMT, Tbx3 and utrophin have been described as intracellular proteins,[13-15] and their detection in plasma indicates their release from cells and limited proteolysis.

Thus, we developed a protocol for collection of plasma, performed 2D-GE and image analysis of samples from cancer and noncancer individuals, and discovered aberrant expression of truncated cSHMT, Tbx3 and utrophin in plasma from breast and ovarian cancer patients.

Aberrant Expression of cSHMT, Tbx3 and Utrophin in Plasma

To confirm and further explore aberrant expression of cSHMT, Tbx3 and utrophin, we performed immunoblotting analysis of plasma samples from a large cohort of patients (Table 1). The validation study was of importance, as not all tryptic peptides from the selected protein spots were used for identification of cSHMT, Tbx3 and utrophin by peptide mass fingerprinting. It is thus possible that other proteins could comigrate in the same spot. The validation by an alternative technique was essential also because peptide mass fingerprinting provided an indication, but did not give 100% confidence of identification. For the validation study, plasma samples were prepared according to the protocol that was used for 2D-GE. However, we used 1D-GE, which allowed comparison of many samples in one gel (FIGS. 2, 3, and 4).

Figure 5:
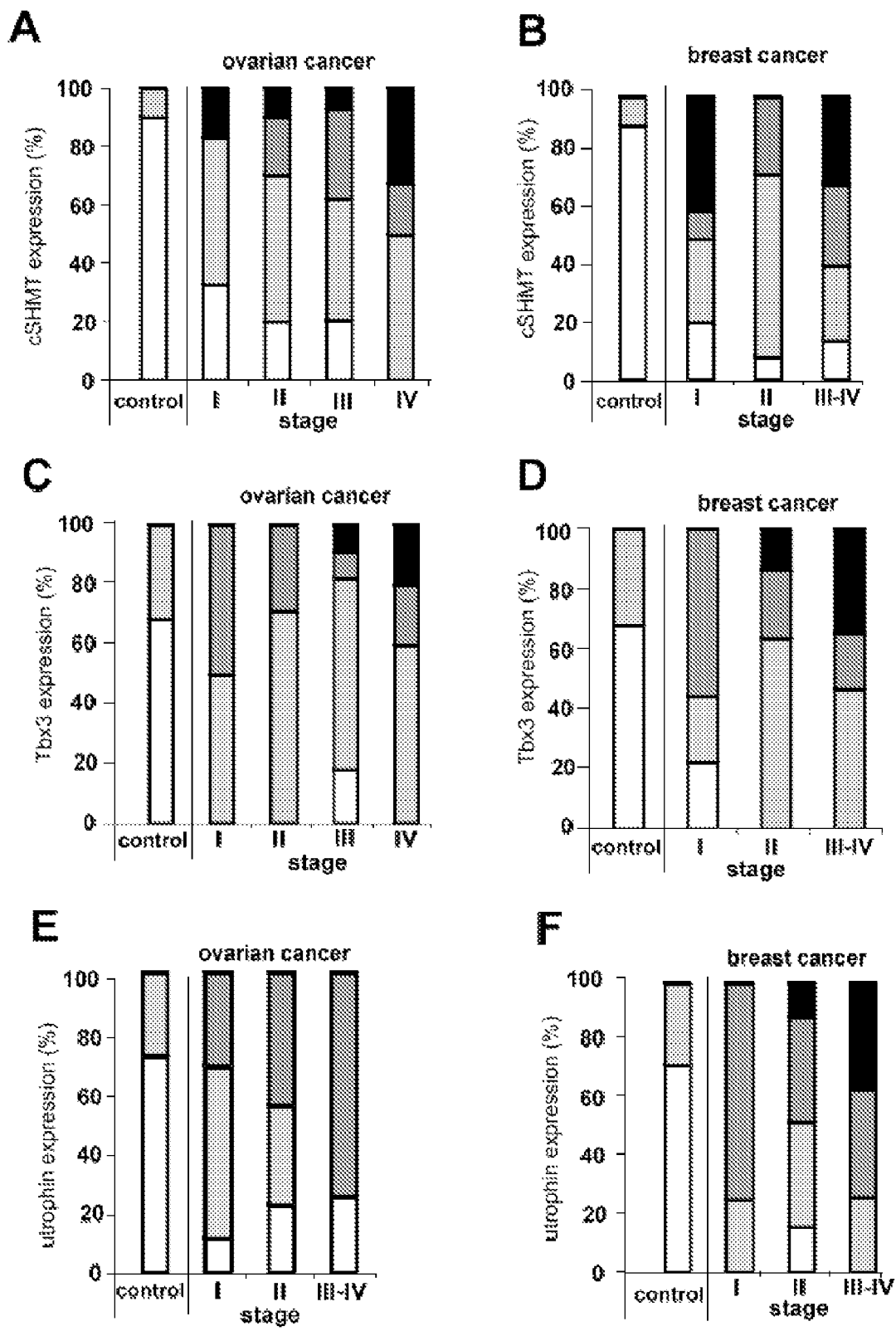
FIGS. 5A-F are graphic depictions of the expression of cSHMT, Tbx3 and utrophin in plasma of patients with various stages of cancer.

Specific antibodies to cSHMT recognized a protein band migrating in plasma samples at the position of 16.5 kDa (FIG. 2A). To control specificity, we found that preincubation of antibodies with specific blocking peptide blocked recognition of this band in a whole-cell extract of MCF7 human breast cancer cells (FIG. 2B). We explored whether incubation of cellular cSHMT with plasma would result in generation of low-molecular-mass product. cSHMT was first detected in COS7 cell extract, and this extract was incubated with fresh plasma (FIG. 2C). We used COS7 cell extract and fresh plasma from a healthy donor, as ethanol-precipitated plasma from patients might have impaired proteolytic activity. Incubation of COS7 cell extracts with fresh plasma led to generation of a cSHMT-specific band of low molecular mass (FIG. 2C). This suggested that the low-molecular-mass cSHMT-specific band is the result of limited proteolysis.

cSHMT-specific protein expression in plasma from the group of healthy and noncancer patients was observed with weak intensity in 3 cases out of 31 (FIGS. 2 and 5). Expression of cSHMT was observed in the samples of patients with stage I of ovarian cancer. At stages II, III and IV of the disease, the frequency of cSHMT detection was similar to that of stage I, or higher (for stage IV). Expression of cSHMT was also stronger, as compared to samples from the control group (FIG. 5A). More than 5-fold more frequent and stronger expression of cSHMT was observed for the breast cancer patients with stage I of the disease, as compared to the control samples (FIG. 5B). The frequency of cSHMT detection in group of patients with stage II and stages III-IV of breast cancer was similar to that observed for patients with stage I (FIG. 5B). Specificity of cSHMT expression was found to be 90%, and sensitivities were 81% for breast cancer and 74% for ovarian cancer.

Antibodies specific to Tbx3 detected proteins of molecular masses of 80 kDa, 62 kDa and approximately 20 kDa, upon expression of Tbx3 in 293T cells (FIG. 3A). As the Tbx3 construct contained an HA-tag, we could confirm the specificity of the anti-Tbx3 antibodies by reprobing the same membrane with anti-HA antibodies. Detection of Tbx3 was abrogated by the specific blocking peptide (FIG. 3A). We explored whether incubation of a cellular extract with plasma would result in generation of a low-molecular-mass product. Tbx3 was first detected in MCF7 cell extract (FIG. 3B), and this extract was incubated with fresh plasma, as described for FIG. 2C. We observed generation of a Tbx3-specific 62 kDa band (FIG. 3B), suggesting that it is the product of a limited proteolysis.

In plasma samples, we observed a strong Tbx3-specific signal from a protein migrating at 62 kDa (FIG. 3C), and a much weaker signal from a protein migrating at approximately 20 kDa. As both 62 kDa and 20 kDa proteins may be products of limited proteolysis of the full-length Tbx3 (FIGS. 3A and B), we studied the expression of the 62 kDa form of Tbx3. It is possible that the 62 kDa form of Tbx3 comigrated with serum albumin, and therefore was not detected in 2D-GE, while in the immunoblotting experiment the 62 kDa form was the most prominent. We observed weak expression of Tbx3 in 30% of samples from noncancerous patients (FIG. 3C). In plasma samples from cancer patients, Tbx3 was detected in all cases of stage I of ovarian cancer, and in 80% of patients with breast cancer (FIGS. 5C and D). Tbx3 was also detected in all samples from patients with advanced breast cancers (FIG. 5D). In all cancer cases, the levels of Tbx3 expression were elevated (FIGS. 5C and D). Specificity of Tbx3 expression was 68%, and sensitivities were 98% for breast cancer and 90% for ovarian cancer cases.

Immunoblotting with antibodies specific to utrophin identified a strong protein band of molecular mass approximately 30 kDa in the plasma samples of cancer patients (FIG. 4A). This migration position corresponds to the migration position of the protein spot in 2D gels, in which utrophin was identified. As we explored for cSHMT and Tbx3 (FIGS. 2C and 3B), we also studied generation of a 33 kDa utrophin-specific band (FIG. 4B). We observed a strong generation of 33 kDa band recognized by antiutrophin antibodies upon incubation of cell extract with plasma (FIG. 4B).

We observed weak expression of utrophin in a number of plasma samples from noncancer patients (FIG. 4C). However, in samples from cancer patients expression of utrophin was significantly stronger and more frequent (FIGS. 5E and F). In the breast cancer samples, utrophin was detected in all samples of stage I, with increased level of expression in more than 75% of the cases (FIGS. 5E and F). In the ovarian cancer samples, frequency of utrophin expression increased to more than 80% of the cases, with an increased level of protein expression (FIG. 5E). Specificity of utrophin expression was 83%, and sensitivities were 72% for breast cancer and 100% for ovarian cancer cases.

cSHMT, Tbx3 and utrophin have been described as intracellular proteins.[13-15] Their detection in plasma, as truncated proteins, suggests that they were released from cells. The molecular mechanisms of tumorigenesis may vary between tumor cells of the same type of cancer. This explains why expression patterns of a single separately taken protein (FIGS. 2, 3 and 4) did not correlate to 100% with a type of cancer, or a stage of disease. Thus, combined patterns of expression of cSHMT, Tbx3 and utrophin in plasma may be included in multifactorial prediction of the early stages of cancer.

Figure 6:
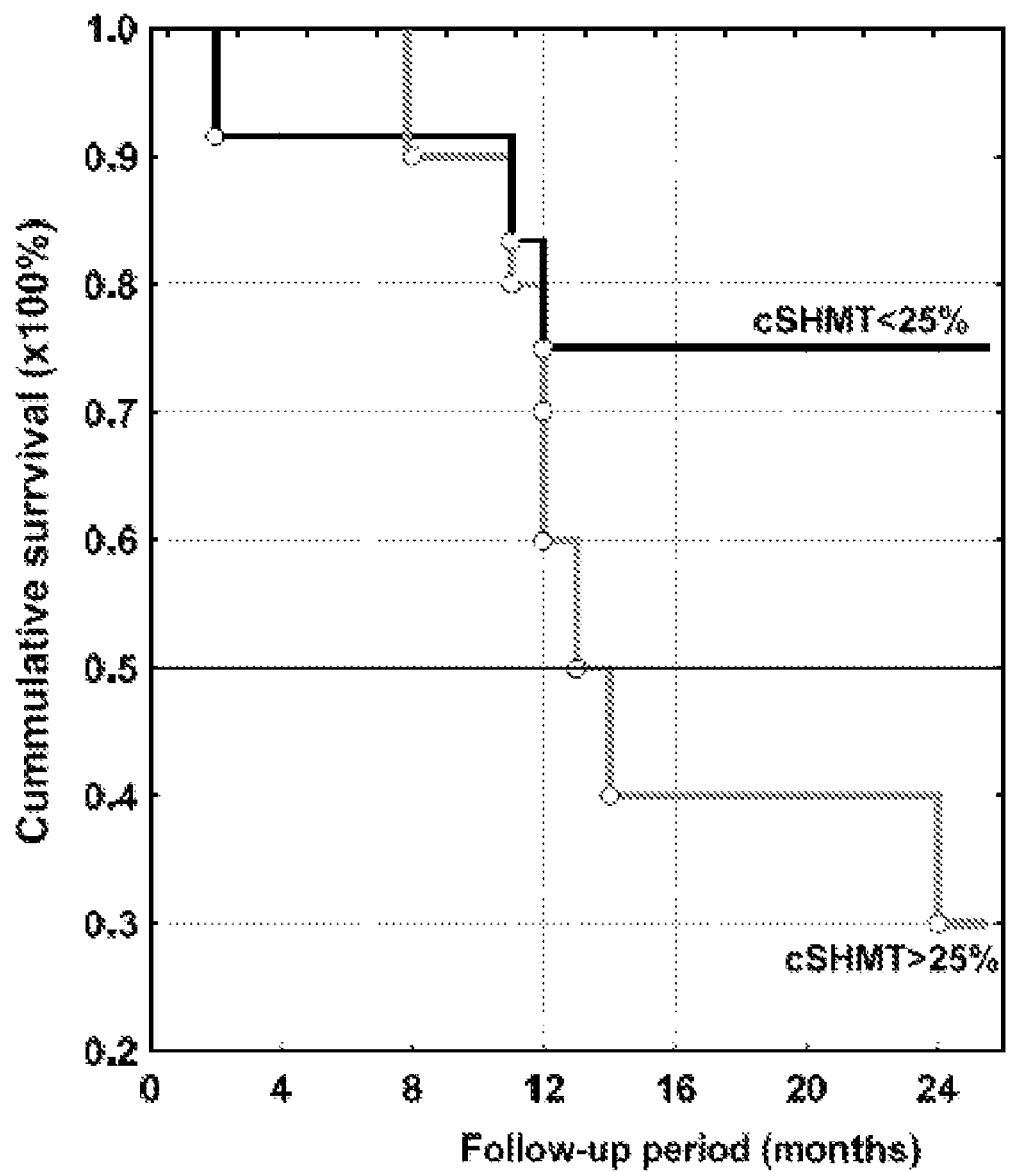
FIG. 6 is a graphic depiction of the correlation between expression of cSHMT in plasma and survival time of ovarian cancer patients.

Twenty-four-month overall survival of ovarian cancer patients was higher in the group with negative and low expression of cSHMT in plasma (4 patients died out of 12 followed), as compared to the patients with moderate and strong expression of cSHMT (5 patients died out of 7 followed; FIG. 6). During the follow-up period, 4 breast cancer patients with stage III died, while the other 75 patients were alive by November of 2004, i.e. more than 24 months after the initial diagnosis.

In a follow-up study, the overall survival of 39 ovarian cancer patients over a 48-month period was correlated with cSHMT expression in plasma. As can be seen in FIG. 7, higher levels of cSHMT expression corresponded to much lower rates of survival. After 48 months, the survival rate of patients with low levels of expression was 80%, whereas after only 36 months, the survival rate of patients with moderate expression was only about 15%. In addition, the prognostic factor for cSHMT expression and survival of ovarian cancer patients was determined by multivariate analysis (Cox regression model). By this analysis also (see Table 3), a strong correlation was demonstrated between level of cSHMT expression in plasma and overall survival of ovarian cancer patients.

Strong correlations between Tbx3 and utrophin expression in plasma and overall survival of breast cancer patients were also observed.

The overall survival of 50 breast cancer patients over a 48-month period was correlated with Tbx3 expression in plasma. As can be seen in FIG. 8, the survival rate of patients with moderate levels of expression was dramatically lower than the rate for patients with low levels of expression.

Similarly, the overall survival of 55 breast cancer patients over a 48-month period was correlated with utrophin expression in plasma. Again, as can be seen in FIG. 9, the survival rate of patients with moderate levels of expression was dramatically lower than the rate for patients with low levels of expression.

In addition, the prognostic factors for Tbx3 and utrophin expression in plasma and survival of breast cancer patients were determined by multivariate analysis (Cox regression model). By this analysis also (see Table 4), strong correlations were demonstrated both 1) between levels of Tbx3 expression and breast cancer survival and 2) between levels of utrophin expression and breast cancer survival.

The data demonstrate a correlation between expression in plasma of each of the three markers and truncated forms thereof and the stage of cancer, as well as a correlation between expression of the markers and aggressiveness of the disease.

TABLE 1

Expression (%) of cSHMT, Tbx3, utrophin in plasma of control (A), and ovarian and breast cancer patients (B)

A)

| Patient | Diagnosis | cSHMT expression, % | Tbx3 expression, % | utrophin expression, % |
|---|---|---|---|---|
| A | Healthy | 0 | — | — |
| B | Healthy | 0 | — | — |
| C | cervical epithelium dysplasia | 0 | — | — |
| D | cervical epithelium dysplasia | 0 | — | — |
| E | cervical epithelium dysplasia | 0 | — | — |
| F | cervical epithelium dysplasia | 0 | — | — |
| G | serous cyst of left ovary | 0 | — | — |
| H | serous cyst of left ovary | 0 | — | — |
| I | fibromyoma of uterus | 0 | — | — |
| J | serous cystadenoma of ovary | 0 | — | — |
| K | fibroadenoma of right breast | 0 | — | — |
| L | fibroadenoma of left breast | 0 | — | — |
| 2 | serous cyst of ovary | 0 | 0 | 0 |
| 4 | dermoid cyst, adenofibroma of ovary | 0 | 0 | 0 |
| 5 | adenocystous polyp of endometrium | 0 | 9 | 0 |
| 10 | fibromyoma of uterus | 0 | 10 | 0 |
| 13 | fibrous mastopathy of breast | 0 | 7 | 18 |
| 17 | folioid fibromyoma of breast | 0 | 10 | 0 |
| 18 | proliferative mastopathy with sclerotic adenosis | 0 | 13 | 0 |
| 21 | endometrioid cyst of ovary | 0 | 12 | 0 |
| 23 | fibrous mastopathy, chronichal mastitis | 0 | 10 | 8 |
| 29 | Healthy | 0 | 9 | 18 |
| 33 | fibroadenomatosis with focal sclerotic adenosis of breast | 0 | 8 | 26 |
| 52 | mucinous cystadenoma of ovary | 0 | 10 | 36 |
| 25 | serous cystadenoma of ovary | 0 | 10 | 21 |
| 47 | fibroadenoma of breast | 0 | 15 | 0 |
| 79 | follicular cyst of ovary, chronichal salpingitis | 5 | 13 | — |
| 82 | cylioepithelial cyst of ovary | 7 | 14 | 0 |
| 104 | serous cyst of ovary | 4 | 11 | 0 |
| 108 | interrupted tubal pregnancy | 10 | 8 | 0 |
| 117 | lipoma of breast | 8 | 9 | 0 |

B)

| Patient | Diagnosis | pT | pN | pM | pG | stage | cSHMT expression, % | Tbx3 expression, % | utrophin expression, % |
|---|---|---|---|---|---|---|---|---|---|
| a | ovarian cancer | 3C | 0 | 0 | | III | 26 | — | — |
| b | ovarian cancer | 2 | 0 | 1 | | IV | 25 | — | — |
| c | ovarian cancer | 2 | 0 | 0 | | II | 14 | — | — |
| d | ovarian cancer | 1C | 0 | 0 | 2 | IC | 23 | — | — |
| e | ovarian cancer | 1C | 0 | 0 | 2 | IC | 10 | — | — |
| f | ovarian cancer | 3C | 0 | 0 | | IIIC | 32 | — | — |
| g | ovarian cancer | 3C | 0 | 0 | | IIIC | 17 | — | — |
| 1 | ovarian cancer | 3 | 0 | 0 | | III | 31 | 11 | 0 |
| 3 | ovarian cancer | 3 | 0 | 0 | | III | 22 | 19 | 0 |
| 20 | ovarian cancer | 2 | 0 | 0 | | II | 35 | 23 | 0 |
| 27 | ovarian cancer | 2 | 0 | 1 | | IV | 17 | 15 | 0 |
| 39 | ovarian cancer | 2 | 0 | 0 | | II | 12 | 13 | 41 |
| 40 | ovarian cancer | 3A | 0 | 0 | | IIIA | 93 | 12 | 24 |
| 41 | ovarian cancer | 2 | 0 | 0 | | II | 66 | 12 | 27 |
| 48 | ovarian cancer | 3 | 0 | 0 | | III | 29 | 15 | — |
| 50 | ovarian cancer | 3A | o | 0 | 1 | III | 18 | 16 | — |
| 51 | ovarian cancer | x | x | 1 | | IV | 63 | 18 | — |
| 53 | ovarian cancer | 2 | 0 | 0 | | II | 29 | 18 | 67 |

TABLE 1-continued

Expression (%) of cSHMT, Tbx3, utrophin in plasma of control (A), and ovarian and breast cancer patients (B)

| # | Type | | | | | | | | |
|---|---|---|---|---|---|---|---|---|---|
| 55 | ovarian cancer | x | x | 1 | | IV | 6 | 15 | 51 |
| 57 | ovarian cancer | x | x | 1 | | IV | 33 | 57 | 66 |
| 78 | ovarian cancer | x | x | x | | x | 12 | 0 | 57 |
| 80 | ovarian cancer | 1A | 0 | 0 | 1 | IA | 21 | 25 | 61 |
| 83 | ovarian cancer | 3 | 0 | 0 | | III | 0 | 7 | 58 |
| 84 | ovarian cancer | 3C | 0 | 0 | | III | 0 | 10 | 57 |
| 86 | ovarian cancer | 2B | 0 | 0 | 2 | IIB | 7 | 28 | 49 |
| 88 | ovarian cancer | 2B | 0 | 0 | | II | 11 | — | 32 |
| 89 | ovarian cancer | 2B | 0 | 0 | | II | 17 | 57 | 36 |
| 90 | ovarian cancer | 3B | 0 | 0 | 1 | III | — | — | 32 |
| 93 | ovarian cancer | 3 | 0 | 1 | | IV | 55 | 71 | 54 |
| 107 | ovarian cancer | 3 | 0 | 0 | | III | 48 | 79 | — |
| 116 | ovarian cancer | 3C | 0 | 0 | | IIIC | 23 | 28 | — |
| 118 | ovarian cancer | 1A | 0 | 0 | 1 | IA | 0 | 41 | — |
| 120 | ovarian cancer | 2B | 0 | 0 | | II | 0 | 45 | 40 |
| 123 | ovarian cancer | 3C | 0 | 0 | | III | 25 | 60 | 43 |
| 134 | ovarian cancer | 3 | 0 | 0 | | III | 14 | 33 | 30 |
| 135 | ovarian cancer | 2A | 0 | 0 | | II | 0 | 36 | 23 |
| 141 | ovarian cancer | 1C | 0 | 0 | | IC | 0 | 33 | — |
| 142 | ovarian cancer | 1C | 0 | 0 | | IC | 54 | 54 | — |
| 143 | ovarian cancer | 3C | 0 | 0 | | III | 0 | — | 44 |
| g1 | breast cancer | 4 | 2 | 0 | | III | 43 | — | — |
| g2 | breast cancer | 1 | 0 | 0 | | I | 62 | — | — |
| g3 | breast cancer | 4 | 2 | 0 | | IV | 18 | — | — |
| g4 | breast cancer | 2 | 0 | 0 | | II | 22 | — | — |
| g5 | breast cancer | 2 | 0 | 0 | | II | 34 | — | — |
| g6 | breast cancer | 2 | 0 | 0 | | II | 21 | — | — |
| g7 | breast cancer | 1 | 0 | 0 | | II | 24 | — | — |
| g8 | breast cancer | 2 | 1 | 0 | | II | 35 | — | — |
| g9 | breast cancer | 1 | 0 | 0 | | I | 67 | — | — |
| g10 | breast cancer | 2 | 0 | 0 | 3 | II | 43 | — | — |
| g11 | breast cancer | 2 | 0 | 0 | 3 | IIA | 15 | — | — |
| g12 | breast cancer | x | x | 1 | | IV | 13 | — | — |
| g14 | breast cancer | 1 | 0 | 0 | | I | 21 | — | — |
| g15 | breast cancer | 1 | 2 | 0 | 3 | III | 16 | — | — |
| g16 | breast cancer | 2 | 0 | 0 | | II | 6 | — | — |
| g17 | breast cancer | 2 | 0 | 0 | 2 | II | 7 | — | — |
| g19 | breast cancer | 2 | 0 | 1 | | IV | 0 | — | — |
| g20 | breast cancer | 1 | 0 | 0 | 1 | I | 0 | — | — |
| g21 | breast cancer | is | 0 | 0 | | 0(Cr is) | 6 | — | — |
| g22 | breast cancer | 2 | 0 | 0 | 3 | II | 4 | — | — |
| 6 | breast cancer | 2 | 1 | 0 | | IIA | — | — | 33 |
| 7 | breast cancer | 2 | 1 | 0 | | IIA | — | — | 46 |
| 8 | breast cancer | 2 | 1 | 0 | | IIA | 6 | 52 | — |
| 11 | breast cancer | 1 | 0 | 0 | | I | 14 | — | — |
| 12 | breast cancer | 2 | 1 | 0 | | IIB | 17 | — | 75 |
| 14 | breast cancer | 2 | 1 | 0 | | III | 17 | 20 | 85 |
| 15 | breast cancer | 1 | 1A | 0 | 2 | II | 27 | 18 | 52 |
| 16 | breast cancer | 2 | 0 | 0 | | IIA | 38 | 20 | 20 |
| 22 | breast cancer | 2 | 1 | 0 | 2 | IIB | 24 | 20 | 18 |
| 30 | breast cancer | 2 | 2 | 0 | 3 | IIIA | 19 | 30 | 21 |
| 31 | breast cancer | 1 | 0 | 0 | 1 | I | 51 | 9 | 18 |
| 32 | breast cancer | 2 | 1 | 0 | | IIB | 20 | 15 | 15 |
| 34 | breast cancer | x | x | x | | x | 52 | 40 | 17 |
| 35 | breast cancer | x | x | x | 2 | x | 24 | 19 | 20 |
| 36 | breast cancer | 4 | 0 | 0 | 3 | IV | 22 | 42 | 14 |
| 42 | breast cancer | x | x | x | | x | 28 | 116 | 15 |
| 44 | breast cancer | 2 | 1 | 0 | 2 | II | 13 | 150 | 18 |
| 45 | breast cancer | 2 | 1 | 0 | | IIIA | 0 | 92 | 21 |
| 46 | breast cancer | x | x | x | 2 | x | 23 | 136 | 21 |
| 58 | breast cancer | 2 | 1 | 0 | 2 | III | — | 57 | 19 |
| 59 | breast cancer | x | x | x | | x | — | 51 | — |
| 61 | breast cancer | 2 | 0 | 0 | 2 | II | 0 | 57 | 30 |
| 62 | breast cancer | 2 | 0 | 0 | 2 | II | — | 31 | 32 |
| 64 | breast cancer | 2 | 0 | 0 | | II | — | 36 | 46 |
| 65 | breast cancer | 2 | 0 | 0 | 2 | II | — | 19 | 52 |
| 66 | breast cancer | 2 | 1 | 0 | 2 | III | — | 27 | 44 |
| 69 | breast cancer | is | 0 | 0 | | 0(Cr is) | 12 | 24 | 53 |
| 70 | breast cancer | 2 | 0 | 0 | 2 | II | 17 | 25 | 36 |
| 71 | breast cancer | 2 | 0 | 0 | 2 | II | 9 | — | 17 |
| 72 | breast cancer | 2 | 0 | 0 | 2 | II | 14 | — | 58 |
| 73 | breast cancer | 2 | 0 | 0 | 2 | II | 35 | 62 | 28 |
| 96 | breast cancer | 3 | 0 | 0 | 3 | III | — | 61 | 17 |
| 97 | breast cancer | 2 | 0 | 0 | | IIA | — | 51 | 5 |
| 98 | breast cancer | 2 | 0 | 0 | | IIA | — | 83 | 6 |
| 99 | breast cancer | 2 | 0 | 0 | | IIA | — | 23 | 6 |
| 101 | breast cancer | 2 | 2 | 0 | | IIIA | — | 22 | — |

TABLE 1-continued

Expression (%) of cSHMT, Tbx3, utrophin in plasma of control (A), and ovarian and breast cancer patients (B)

| | | pT | pN | pM | pG | Stage | cSHMT | Tbx3 | Utrophin |
|---|---|---|---|---|---|---|---|---|---|
| 102 | breast cancer | 3 | 1 | 0 | 2 | IIIA | 26 | 25 | 63 |
| 105 | breast cancer | 3 | 0 | 0 | 2 | IIB | 9 | 12 | 55 |
| 106 | breast cancer | 2 | 1 | 0 | 2 | IIB | — | 42 | 66 |
| 109 | breast cancer | 3 | 3 | 0 | 2 | IIIB | — | 36 | 64 |
| 110 | breast cancer | 2 | 1 | 0 | | IIB | 21 | 18 | 60 |
| 111 | breast cancer | 2 | 0 | 0 | | IIA | 18 | 32 | 71 |
| 113 | breast cancer | 2 | 1 | 0 | | IIB | 30 | 37 | 71 |
| 114 | breast cancer | 4 | 2 | 0 | 3 | IIIB | 53 | 106 | 104 |
| 115 | breast cancer | x | x | x | 2 | X | 39 | 61 | 106 |
| 119 | breast cancer | 2 | 0 | 0 | 2 | IIA | — | 52 | 71 |
| 121 | breast cancer | 3 | 1 | 0 | 2 | IIIB | — | 58 | 66 |
| 122 | breast cancer | 1 | 1 | 0 | 2 | III | 76 | — | 79 |
| 124 | breast cancer | 2 | 1 | 0 | | III | 51 | — | 93 |
| 125 | breast cancer | 2 | 1 | 0 | 2 | III | 32 | — | 73 |
| 126 | breast cancer | 2 | 1 | 0 | 2 | III | 18 | 91 | 80 |
| 127 | breast cancer | 4 | 0 | 0 | 2 | IIIB | 0 | 85 | 48 |
| 128 | breast cancer | 1 | 0 | 0 | | I | 27 | 45 | 47 |
| 129 | breast cancer | 2 | 1 | 0 | 2 | III | 31 | 32 | 37 |
| 130 | breast cancer | 2 | 1 | 0 | | III | 42 | 39 | 42 |
| 132 | breast cancer | 2 | 0 | 0 | | IIA | 45 | 30 | 43 |
| 133 | breast cancer | 1 | 0 | 0 | | I | 52 | 41 | 52 |
| 138 | breast cancer | 2 | 1 | 0 | 2 | III | 79 | 89 | 60 |
| 139 | breast cancer | 2 | 1 | 0 | 2 | III | 63 | 60 | 76 | pT = tumor size
pN = lymph node metastasis
pM = metastasis
pG = tumor grade

TABLE 2

Identification of cSHMT, Tbx3 and utrophin in protein spots.

| Spot No. a) | Protein b) | Probability b) | Z value b) | Sequence coverage (%) b) | NCBI accession number b) | Theoretical value c) pI | Theoretical value c) Mr (kDa) | Experimental value c) pI | Experimental value c) Mr (kDa) |
|---|---|---|---|---|---|---|---|---|---|
| s502 | Cytosolic serine hydroxymethyl-transferase | 9.9e−01 | 0.72 | 12 | Y14487 | 6.9 | 38.7 | 6.0 | 18.0 |
| s515 | Tbx3 | 9.3e−01 | 0.58 | 12 | AF002228 | 8.4 | 52.1 | 5.3 | 17.0 |
| s385 | Utrophin | 1.0e+000 | 1.23 | 13 | X69086 | 5.9 | 68.8 | 5.5 | 30.0 | a) Spot numbers are as annotated by the image analysis.
b) Protein names, probability, Z, sequence coverage and NCBI accession numbers are as obtained in a search of NCBI database with ProFound search engine.
c) Theoretical and experimental values of pI and molecular mass are indicated. Experimental values were calculated from migration positions of proteins in 2D gels.

TABLE 3

Independent prognostic factors of the survival of ovarian cancer patients (n = 39), multivariate analysis (Cox regression model).

| Prognostic factor | P |
|---|---|
| cSHMT expression in plasma | 0.013 |
| Tbx3 expression in plasma | 0.560 |
| Utrophin expression in plasma | 0.334 |

$\chi^2 = 26.79$,
p = 0.0015.
(See also annotations to Table 4)

TABLE 4

Independent prognostic factors (*) of the survival of breast cancer patients (n = 76), multivariate analysis (Cox regression model).

| Prognostic factor | P** |
|---|---|
| cSHMT expression in plasma | 0.159 |
| Tbx3 expression in plasma | 0.019 |
| Utrophin expression in plasma | 0.025 |

$\chi^2 = 20.72$,
p = 0.0232
(*) Independent prognostic value for overall survival of breast cancer patients was calculated for cSHMT, Tbx3 and utrophin expression in blood plasma and the following parameters: pT 1-4 (tumor size), pN 0-2 (lymph node metastasis), M 0-1 (metastasis), pG 1-3 (tumor grade), stage (I-IV), tumor histology type (lobular and ductal), age (below and over 40).
**P, prognostic factor significance; in bold - significant values.

As shown by the disclosure herein, it has been discovered that increased expression in plasma of cSHMT, Tbx3, utrophin and truncated forms thereof, either alone or in combinations, has a strong correlation with increased incidence of ovarian and breast cancer, as well as decreased time and chance of survival for cancer patients.

The present application describes not only the discovery of these correlations but also the discovery of a number of truncated forms of cSHMT, Tbx3 and utrophin. The present invention is directed not only to the specific truncated forms mentioned herein but to all truncated forms of these markers that may be produced in conjunction with the onset of ovarian and/or breast cancer. These truncated forms are readily visualized, identified and quantitated by the techniques described herein. Furthermore, the actual sequences of the truncated forms may readily be derived by one of skill in the art by employment of standard techniques of peptide and amino acid analysis (see, for example, Proteins and Proteomics, Richard J. Simpson, Cold Spring Harbor Laboratory Press (2003) and Modern Protein Chemistry: Practical Aspects, G. C. Howard and W. E. Brown, Eds., CRC Press, Boca Raton, Fla. (2002)) and the prior knowledge of the primary structures of the full-length forms of the proteins.

The present invention further encompasses antibodies raised against the full-length and truncated forms of the protein markers, which antibodies are necessary for the practice of the diagnostic and prognostic methods described herein. Such antibodies may be produced by any of the techniques well known to one of skill in the art. (See, for example, Monoclonal Antibodies: Methods and Protocols, R. Rose and M. Albitar, Eds., Humana Press, 1st Edition (2007) and Antibodies: A Laboratory Manual, Harlow and Lane, Cold Spring Harbor Laboratory Press (2003).) Although monoclonal antibodies are preferred for the practice of the invention, the invention also encompasses polyclonal antibodies of suitable specificity.

The discovery of the correlations set forth herein and the discovery of the truncated forms of the protein markers also provide the means for diagnosing ovarian and/or breast cancer and for predicting longevity and chance of survival of patients with these cancers. Accordingly, another aspect of the present invention are the diagnostic and prognostic methods disclosed herein in connection with ovarian and/or breast cancer. These methods comprise the steps of a) obtaining a plasma sample from a patient; b) testing among the proteins in the sample for the presence and amount of one or more of cSHMT, Tbx3, utrophin and truncated forms thereof, and either, for diagnostic purposes, c) using the level(s) of the marker(s) detected in a patient of unknown status to determine the likelihood or not of the patient having ovarian and/or breast cancer or, for prognostic purposes, d) using the level(s) of the marker(s) detected in a patient already known to have ovarian and/or breast cancer to determine the optimal regimen of treatment, predict the patient's response to the treatment and to predict the likelihood or duration of survival.

Still further, the invention encompasses kits comprising one or more antibodies generated against cSHMT, Tbx3 and utrophin, and against truncated forms thereof associated with the onset of ovarian and/or breast cancer, which kits are useful in the diagnosis and prognosis of ovarian and/or breast cancer.

The present invention has added three proteins, and truncated forms thereof, to the list of markers which can be used for creation of a diagnostic and prognostic microarray in connection with ovarian and/or breast cancer. As borne out by the showing herein, the novel markers of the present invention may be used either singularly or, in a multiparameter diagnostic or prognostic approach, in various combinations. It is further expected that one or more of the inventive markers can be used in combination with other, previously known markers in a multiparameter diagnostic or prognostic approach. The additional markers may be proteinaceous or not and may have their origins in either plasma or tissue. Nonlimiting examples of such markers are CA125, CA15-3, CEA, RS/DJ1, apolipoprotein A1, transthyretin, inter-α trypsin inhibitor heavy chain H4, haptoglobin-1 and kallikrein; lysophosphatidic acid and DNA[3,20] and estrogen receptors such as ErbB2/neu and Ki-67.[21]

The invention is thus also directed to microarrays of proteins and other markers for use in the diagnosis and/or prognosis of ovarian and/or breast cancer. These microarrays comprise one or more markers selected from cSHMT, Tbx3, utrophin and truncated forms thereof in combination with one more previously known markers as exemplified above.

REFERENCES

1. Anderson N L, Anderson N G. The human plasma proteome: history, character and diagnostic prospects. Mol. Cell. Proteomics 2002; 1:845-67.
2. Anderson N L, Polanski M, Pieper R, Gatlin T, Tirumalai R S, Conrads T P, Veenstra T D, Adkins J N, Pounds J G, Fagan R, Lobley A. The human plasma proteome: a nonredundant list developed by combination of four separate sources. Mol. Cell. Proteomics 2004; 3:311-26.
3. Sidransky D. Emerging molecular markers of cancer. Nature Rev. 2002; 2:210-19.
4. Le Naour F, Misek D E, Krause M C, Deneaux L, Giordano T J, Scholl S, Hanash S M. Proteomics-based identification of RS/DJ-1 as a novel circulating tumor antigen in breast cancer. Clin. Cancer Res. 2001; 7:3328-35.
5. Cohen L S, Escobar P F, Scharm C, Glimco B, Fishman D A. Three-dimensional power Doppler ultrasound improves the diagnostic accuracy for ovarian cancer prediction. Gynecol. Oncol. 2001; 82:40-8.
6. Luo L Y, Katsaros D, Scorilas A, Fracchioli S, Bellino R, van Gramberen M, de Bruijn H., Henrik A, Stenman U H, Massobrio M, van der Zee A G J, Vergote I, Diamanidis E P. The serum concentration of human kallikrein 10 represents a novel biomarker for ovarian cancer diagnosis and prognosis. Cancer Res. 2003; 63:807-11.
7. Zhang Z, Bast R C, Yu Y, Li J, Sokoll L J, Rai A J, Rosenzweig J M, Cameron B, Wang Y Y, Meng X Y, Berchuck A, van Haaften-Day C, Hacker F, de Bruijn H W, van der Zee A G, Jacobs I J, Fung E T, Chan D W. Three biomarkers identified from serum proteomic analysis for the detection of early stage ovarian cancer. Cancer Res. 2004; 64:5882-90.
8. Ahmed N, Barker G, Oliva K T, Hoffmann P, Riley C, Reeve S, Smith A I, Kemp B E, Quinn M A, Rice G E. Proteomics-based identification of haptoglobin-1 precursor as a novel circulating biomarker of ovarian cancer. British J. Cancer 2004; 91:129-40.
9. Petricoin III E F, Ardekani A M, Hitt B A, Levine P J, Fusaro V A; Steinberg S M, Mills G B, Simone C, Fishman D A, Kohn E C, Liotta L A. Use of proteomic patterns in serum to identify ovarian cancer. Lancet 2002; 359:572-77.
10. Kanamoto T, Hellman U, Heldin C H, Souchelnytskyi S. Functional proteomics of transforming growth factor-betal-stimulated Mv1 Lu epithelial cells: Rad51 as a target of TGFbeta1-dependent regulation of DNA repair. EMBO J. 2002; 21:1219-30.
11. Lomnytska M, Lukiyanchuk V, Hellman U, Souchelnytskyi S. Functional TGFbeta1-regulated proteins in human endothelial cells identified by two-dimensional gel electrophoresis and mass spectrometry. Proteomics 2004; 4:995-1006.

12. Glantz S. Medico-biological statistics. Moscow: Medicyna, Praktika, 1998. p. 459.
13. Blake D J, Weir A, Newey S E, Davies K E. Function and genetics of dystrophin and dystrophin-related proteins in muscle. Physiol. Rev. 2001; 82:291-329.
14. Chen J, Kyte C, Valcin M, Chan W, Wetmur J G, Selhub J, Hunter D J, Ma J. Polymorphisms in the one-carbon metabolic pathway, plasma folate levels and colorectal cancer in a prospective study. Int. J. Cancer 2004; 110:617-20.
15. Bamshad M, Lin R C, Law D J, Watkins W C, Krakowiak P A, Moore M E, Franceschini P, Lala R, Holmes L B, Gebuhr T C, Bruneau B G, Schinzel A, Seidman J G, Seidman C E, Jorde L B. Mutations in human TBX3 alter limb, apocrine and genital development in ulnar-mammary syndrome. Nat. Genet. 1997; 16:311-15.
16. van't Veer L, Dai H, van de Vijver M J, He Y D, Hart A A, Mao M, Peterse H L, van der Kooy K, Marton M J, Witteveen A T, Schrieber G J, Kerkhoven R M, et al. Gene expression profiling predicts clinical outcome of breast cancer. Nature 2002; 415:530-36.
17. Kreunin P, Urquidi V, Lubman D M, Goodison S. Identification of metastasis-associated proteins in a human tumor metastasis model using the mass-mapping technique. Proteomics 2004; 4:2754-65.
18. Brummelkamp T R, Kortlever R M, Lingbeek M, Trettel F, MacDonald M E, van Lohuizen M, Bernards R. TBX3, the gene mutated in ulnar-mammary syndrome, is a negative regulator of p19ARF and inhibits senescence. J. Biol. Chem. 2002; 277:6567-72.
19. Henry M D, Cohen M B, Campbell K P. Reduced expression of dystroglycan in breast and prostate cancer. Hum. Pathol. 2001; 32:791-95.
20. Jones M B, Krutzsch H, Zhao Y, Liotta L A, Kohn E C, Petricoin III E F. Proteomic analysis and identification of new biomarkers and therapeutic targets for invasive ovarian cancer. Proteomics 2002; 2:76-84.
21. Esteva F J, Hortobagy G N. Prognostic molecular markers in early breast cancer. Breast Cancer Res. 2004; 6:109-18.

Legends for FIGS. 1-6

FIG. 1. Detection of cSHMT, Tbx3 and utrophin in two-dimensional gels of plasma samples. (A) The scheme of the study is presented. Plasma was prepared from collected blood, and proteins were precipitated with ethanol. 100 µg of plasma proteins were separated by 2D-GE. Differentially expressed proteins were identified by MALDI TOF MS. Samples from a large cohort of patients were tested by immunoblotting with antibodies specific to selected proteins. (B) An image of a 2D gel is shown to illustrate quality of protein resolution. The gel represents a control sample from a non-cancer patient. The pH gradient is indicated on the top of the gel, and migration positions of molecular mass markers are indicated on the side of the gel. Areas of migration of cSHMT, Tbx3 and utrophin are indicated by squares. (C) Areas of migration of cSHMT (upper panels), Tbx3 (middle panels) and utrophin (lower panels) in 2D gels of control (left row), ovarian cancer (middle row) and breast cancer (right row) samples are shown. Protein spots containing cSHMT, Tbx3 and utrophin are indicated by circles. Arrowheads indicate migration positions of reference protein spots.

FIG. 2. Detection of cSHMT in plasma samples by immunoblotting. (A) Samples were prepared as for 2D-GE, and were subjected to 1D SDS-PAGE, transferred onto membrane and immunoblotted with anti-cSHMT antibodies, as described earlier herein. Migration positions of a protein with molecular mass which corresponds to the cSHMT identified in 2D gels are indicated by arrows in upper panels. IgG-specific protein bands, detected in all samples after reprobing the same membranes with antihuman IgG are indicated by arrows in lower panels. (B) Specific blocking peptide abrogated recognition of a protein migrating at the position of 16.5 kDa. The whole-cell extract from MCF7 cells was subjected to SDS-PAGE and immunoblotting with antibodies to cSHMT which were preincubated or not with blocking peptide, as indicated. Migration positions of a protein with molecular mass which corresponds to the cSHMT identified in 2D gels is indicated by an arrow. (C) A low-molecular-mass cSHMT-specific band was detected after incubation of COS7 cell extract with fresh plasma from a healthy individual (COS7+plasma). Aliquots of cell extract (COS7), plasma only (plasma), and mixture of cell extract with plasma in the ratio 1:3, respectively (1:3; 1:3 precipitate) were immunoblotted with anti-cSHMT antibodies. The "1:3 precipitate" fraction shows the mixture of cell extract and plasma prepared according to the plasma preparation protocol described earlier herein. The arrow shows a cSHMT-specific protein band which increased after incubation of the cell extract with plasma. Migration positions of molecular mass markers are indicated on the side of images. Annotations of samples in panel (A) are as in Table 1. Representative experiments with randomly selected samples out of 4 (A) and 3 (B, C) performed are shown.

FIG. 3. Detection of Tbx3 in plasma samples by immunoblotting. (A) Specific blocking peptide abrogated recognition by antibodies specific to Tbx3 of prominent proteins with molecular masses of 80 kDa and 62 kDa, and of a less strongly expressed protein of 20 kDa. Arrows indicate the proteins. (B) A 62 kDa Tbx3-specific band was detected after incubation of MCF7 cell extract with fresh plasma from a healthy individual (MCF7+plasma). Aliquots of cell extract (MCF7), plasma only (plasma), and mixture of cell extract with plasma in the ratio 1:3, respectively (1:3; 1:3 precipitate) were immunoblotted with anti-Tbx3 antibodies. The "1:3 precipitate" fraction shows the mixture of cell extract and plasma prepared according to the protocol described earlier herein. The arrow shows a Tbx3-specific protein band which increased after incubation of the cell extract with plasma. Migration positions of molecular mass markers are indicated on the side of images. (C) Plasma samples were prepared as for 2D-GE, and were subjected to 1D SDS-PAGE, transferred onto membrane and immunoblotted with anti-Tbx3 antibodies, as described earlier herein. Migration positions of a protein with molecular mass which corresponds to the truncated Tbx3 are indicated by arrows in upper panels. IgG-specific protein bands, detected in all samples after reprobing the same membranes with antihuman IgG, are indicated by arrows in lower panels. Annotations of samples are as in Table 1. Representative experiments with randomly selected samples out of 4 (C) and 2 (A, B) performed are shown.

FIG. 4. Detection of utrophin in plasma samples by immunoblotting. (A) Expressions of utrophin truncated isoform in plasma samples from control, ovarian and breast cancer groups are shown. The arrow indicates migration position of the utrophin isoform. The arrowhead indicates migration position of a nonspecific protein. Migration positions of molecular mass markers are indicated on the side of images. (B) A 33 kDa utrophin-specific band was detected after incubation of 293T cell extract with fresh plasma from a healthy individual (293T+plasma). Samples were prepared as in FIG. 2C. Notably, aliquots of cell extract (293T), plasma only (plasma), and mixture of cell extract with plasma in the ratio 1:3, respectively (1:3; 1:3 precipitate) were immunoblotted with anti-utrophin antibodies. The "1:3 precipitate" fraction shows the mixture of cell extract and plasma prepared according to the protocol described earlier herein. The arrow shows a utrophin-specific protein band which increased after incubation of the cell extract with plasma. (C) Plasma samples were prepared as for 2D-GE, and were subjected to 1D SDS-PAGE, transferred onto membrane and immunoblotted with antiutrophin antibodies, as described earlier herein. Migration positions of a protein with molecular mass which corresponds to the utrophin truncated isoform are indicated by arrows in upper panels. IgG-specific protein bands, detected in all samples after reprobing the same membranes with anti-human IgG are indicated by arrows in lower panels. Annotations of samples are as in Table 1. Representative experiments with randomly selected samples out of 4 (C), 3 (A) and 2 (B) performed are shown.

FIG. 5. Expression of cSHMT, Tbx3 and utrophin in samples of patients with various stages of cancer. Expression of cSHMT, Tbx3 and utrophin was normalized to intensities of non-specific bands which were present in all samples, and was calculated as a relative intensity as described earlier herein. Distributions of relative intensities of protein expressions for various stages of patients with ovarian (A, C, E) and breast (B, D, F) cancers are indicated. Expressions of cSHMT (A, B), Tbx3 (C, D) and utrophin (E, F) are shown. For cSHMT, a relative intensity of the specific signal to the IgG band of less than 25% was evaluated as weak (light grey bar), between 26% and 50% as medium (medium grey bar), and higher than 50% as high (dark grey bar). For Tbx3, a relative intensity of up to 40% was evaluated as weak, between 41% and 60% as medium, and higher than 60% as high. For utrophin, a relative intensity of up to 40% was evaluated as weak, between 41% and 70% as medium, and higher than 70% as high. Stages of cancers are indicated in panels. Cutpoints are defined as provided earlier herein.

FIG. 6. Expression of cSHMT correlated with shorter survival of ovarian cancer patients. Comparison of the cumulative overall survival within a 24-month follow-up period of patients of groups with low (<25%; 12 patients, 4 died) and moderate/high (>25%; 7 patients, 5 died) expression of cSHMT in plasma was performed by univariate Kaplan-Meier analysis[12] ($p<0.01$).

What is claimed is:

1. A diagnostic method for ovarian and/or breast cancer in a patient comprising the steps of:
   a) obtaining a plasma sample from the patient;
   b) testing the sample for the presence and amount of one or more protein markers selected from cSHMT, Tbx3, utrophin and truncated forms thereof; and
   c) in the case wherein aberrant levels of one or more of the markers is observed, identifying the patient as likely having ovarian and/or breast cancer or in the case wherein normal or no expression is observed, identifying the patient as free of those cancers.

2. A prognostic method for ovarian and/or breast cancer in a patient known already to have ovarian and/or breast cancer comprising the steps of:
   a) obtaining a plasma sample from the patient;
   b) testing the sample for the presence and amount of one or more protein markers selected from cSHMT, Tbx3, utrophin and truncated forms thereof; and
   c) using the amount of aberrant levels of any or all of the markers as a basis for determining the optimal treatment regimen for the patient, for predicting the patient's response to the treatment and for predicting the likelihood or duration of survival of the patient.

3. The method according to claim 1 or 2 wherein step c) further comprises testing for the presence and amount of one or more previously known markers.

4. The method according to claim 3 wherein the one or more previously known markers are selected from the group consisting of CA125, CA15-3, CEA, RS/DJ1, apolipoprotein A1, transthyretin, inter-α trypsin inhibitor heavy chain H4, haptoglobin-1, kallikrein, lysophosphatidic acid, ErbB2/neu and Ki-67.

* * * * *